United States Patent [19]
Grieve

[11] Patent Number: 4,657,850
[45] Date of Patent: Apr. 14, 1987

[54] SERODIAGNOSIS OF HEARTWORM INFECTION

[75] Inventor: Robert B. Grieve, Radnor, Pa.

[73] Assignee: University Patents, Inc., Westport, Conn.

[21] Appl. No.: 335,179

[22] Filed: Dec. 28, 1981

[51] Int. Cl.$^4$ .................... G01N 33/54; G01N 01/18; G01N 33/545
[52] U.S. Cl. ........................................ 435/7; 436/177; 436/531
[58] Field of Search .............. 435/7, 188, 810; 424/1, 424/8, 12, 85, 88; 23/230 B; 436/825, 531, 177, 811

[56] References Cited

U.S. PATENT DOCUMENTS

| Re. 29,169 | 4/1977 | Schuurs et al. | 435/188 |
| 4,190,328 | 2/1980 | Levine et al. | 23/230 B |
| 4,211,530 | 7/1980 | Goverde et al. | 436/805 |
| 4,322,495 | 3/1982 | Kato | 435/7 |

OTHER PUBLICATIONS

Grieve et al, "Enzyme Linked Immunosorbent Assay for Measurement of Antibody Responses to Dirofilaria Immitis", American Journal of Veterinary Research 42(1), (1-1981), pp. 66-69.

Tanaka, "Measurement of Ascaris-Suum Protein in Sera from Patients with Helminthiasis and Gastrointestinal Diseases by a Specific RIA", Japanese Journal of Parasitology 30(4), (1981), pp. 345-354, Abstract only.

Gittelman et al, "Quantitative Fluorescent Immunoassay for Measurement of Antibody to Dirofilaria-Immitis in Dogs", Journal of Clinical Microbiology 13(2), (1981), pp. 309-311 (abstract).

Sawada et al, "Immunological Studies on Filariasis III: Isolation and Purification of Antigen for Intradermal Skin Test", Japanese Journal of Experimental Medicine 35(2), (1965), pp. 125-132.

Primary Examiner—Charles F. Warren
Assistant Examiner—J. E. Tarcza
Attorney, Agent, or Firm—O'Toole Marshall

[57] ABSTRACT

An improvement in immunological methods for quantitative detection of *Dirofilaria immitis* antibodies in a fluid sample comprising a treatment of the sample with *Toxocara canis*-derived antigens.

4 Claims, No Drawings

SERODIAGNOSIS OF HEARTWORM INFECTION

BACKGROUND OF THE INVENTION

The present invention relates generally to diagnosis of filarial nematode infection and, more specifically, to improvements in immunological methods for quantitative detection of adult stage *Dirofilaria immitis*-associated antibodies in biological fluids.

Filarial nematode infections of humans constitute a worldwide problem estimated to adversely affect the lives of 300 million people. The effects of filarial infection on domesticated animals are correspondingly immense. In the United States alone, millions of dollars are spent each year on treatment of infection in cats, dogs and other pets and agricultural animals. Contributing to the magnitude of the filarial problem is the fact that accurate diagnosis by common diagnostic means remains exceedingly difficult. The absence of reliable procedures for diagnosis of filarial infection has retarded research and development in curative and prophylactic therapy.

*Dirofilaria immitis* is a filarial nematode parasite which, in its adult form, commonly infects the right ventricle, pulmonary artery and adjacent pulmonary vasculature, frequently causing serious tissue damage and death. Infection of dogs with this particular filarial nematode (commonly referred to as "heartworm") is prevalent throughout the world. Patent, or mature *D. immitis* infection in dogs can rather readily be treated through administration of drugs such as thiacetarsamide. Drug therapy is often withheld pending certain diagnosis of *D. immitis* infection, however, because such drugs can be highly toxic to the canine host and the cost of therapy is often prohibitive. Further, the presence or absence of filarial infection may affect the course of treatment of other disease states. As one example, certain drugs useful in treatment of canine intestinal parasites should be avoided because they may be lethal to heartworm, causing fatal embolisms in the recipient animal.

Diagnosis of *D. immitis* infection can be made with certainty where characteristic microfilariae (thread-like *D. immitis* embryonic forms) can be visually detected through examination of body fluids. The presence of detectable numbers of microfilariae indicates that infection has progressed to a state of worm maturity sufficient to cause substantial and frequently irreversible tissue pathology.

Parasitological diagnoses are falsely negative when an infected dog displays a so-called "amicrofilaremic" state. Visual detection of microfilariae will not be possible in early stages of infection in which none or too few of the embryonic organisms are circulating. In the case of single sex infections and in old infections wherein the female worm is no longer reproductively capable, no microfilariae will be formed. Further, an amicrofilaremic state may exist as a result of the host's own protective immune response, which is directed to the microfilarial parasite stage only. Specific antibodies clear the embryos from the host's circulation, leaving the adult worms alive.

Numerous serological procedures have been proposed for detection of filarial infection, but none has been widely accepted as a reliable alternative to parasitological diagnosis. As one example, an assertedly highly specific and sensitive procedure for detection of specific, anti-microfilarial antibodies has been proposed by, e.g., Wong, et al., *Am. J. Vet. Res.*, 40, pp. 414–420 (1979). Briefly put, the test employs intact microfilariae in an indirect fluorescent antibody (IFA) procedure to detect circulating anti-microfilarial antibodies. The procedure thus has an advantage in utility for detecting filarial infection wherein an amicrofilaremic state exists as a result of the infected animal's protective immune response to the presence of the microfilariae. Apart from the fact that the procedure requires expensive fluorometric apparatus generally unavailable in veterinary practice, the test is not effective in diagnosing disease states which are amicrofilaremic as a result of, e.g., single sex infections, and falsely negative results may be nearly as common as in the parasitological procedures. Even when successful, the procedure shares with parasitological detection the disadvantage of ascertaining only relatively advanced disease states.

It is known that the presence of adult nematodes in an infected host does produce a humoral immune response and it has been suggested that reliable assays directed toward detection of adult *D. immitis*-associated antibodies would be exceptionally useful in providing information upon which a therapeutic or prophylactic treatment regimen can be selected.

Proposed enzyme-linked immunosorbent (ELISA) serological assays based on detection of antibodies associated with adult stages of worms have been lacking in reliability and ease of performance. Contributing to the lack of specificity of such procedures is the polyantigenicity of the parasite and the consequently varied immunological response of the host animal. It is widely held, for example, that filarial nematode infection presents the host with an array of antigenic stimuli of varying intensity and duration. Discrete "antigens" which may provoke development of correspondingly discrete circulating antibodies have been associated not only with various body parts of the adult nematode (e.g., the "cuticular" and "cytoplasmic" antigens) but also with nematode growth products ("metabolic" antigens) and, of course, differing growth stages (e.g., the microfilarial-associated antigens).

Crude and semi-purified soluble antigens (like the above-noted "microfilarial" antigens) can be obtained by simple extraction of whole live adult worms and these have been found to be effective in detecting specific adult *D. immitis*-associated antibodies in ELISA assays. Such antigen preparations, however, appear to be additionally cross-reactive with unspecified antibodies present in many serum specimens of both infected and uninfected dogs. Procedures based on the use of adult *D. immitis*-associated antigens have therefore provided falsely positive results.

There exists, therefore, a substantial need to improve the specificity of immunological serodiagnostic assays for adult *D. immitis*-associated antibodies and to reduce the complexity of the procedures so that they can be readily performed in routine veterinary and clinical practice. Such improvements in the serodiagnosis of *D. immitis* infection would aid in the early, accurate detection of infections in which the characteristic microfilariae are circulating in the body fluids and in established amicrofilaremic infections in dogs.

Specifically incorporated by reference herein for the purposes of indicating the background of the invention and illustrating the state of the art are the following publications of the inventor and his co-workers: Grieve, et al., *Am. J. Vet. Res.*, 42, pp. 66–69 (1981); and Grieve, et al., *Int. J. Parasitol* 9, pp. 275–279 (1979).

BRIEF SUMMARY

The present invention provides a novel improvement in detection of *D. immitis* infection in dogs, which improvement increases the specificity of immunological assays for adult *D. immitis*-associated antibodies by decreasing the cross-reactivity of fluid sample constituents with the adult *D. immitis*-associated antigens employed in those assays. More specifically, the present invention involves treating a biological fluid to be employed in an immunological assay for adult *D. immitis*-associated antibody (e.g., ELISA) with a *Toxocara canis*-derived antigen. Treatment with *T. canis*-derived antigen according to the present invention functions to significantly decrease falsely positive results of immunological assays for adult *D. immitis*-associated antibodies without correspondingly generating falsely negative results. Put another way, the sample treatment step of the invention unexpectedly operates to clear the sample of non-*D. immitis* immune constituents which cross-react with *D. immitis* antigen preparations without also depleting the sample of specific adult *D. immitis*-associated antibodies.

The present invention's treatment step has proven successful in the testing of whole blood fluid samples as well as serum.

Other aspects and advantages of the present invention will become apparent upon consideration of the following detailed description.

DETAILED DESCRIPTION

*T. canis* is an intestinal roundworm which commonly infects puppies up to five months of age. When older dogs ingest *T. canis* larvae, the larvae will migrate from the intestine to extraintestinal tissues where they remain in an arrested state of development. These arrested larvae will slowly metabolize, generating antigens, and may live for years resulting in a latent infection with no obvious symptoms. [See, e.g., Sprent, *Parasitology*, 64, pp. 565–567 (1978)]. Such a latent *T. canis* infection in adult dogs may be sufficient to arouse a humoral immune response in the host with the result that most adult dogs have circulating *T. canis*-associated antibodies. Crude and semi-purified *D. immitis*-associated antigens employed in ELISA and other immunological assays apparently contain one or more immunologically active sites which react with the *T. canis*-associated antibodies as well as *D. immitis*-associated antibodies and thereby produce an inaccurate or falsely positive assay for dirofilariasis.

Remarkably, there appears to be no corresponding cross-reactivity of *T. canis*-derived antigen preparations with specific adult *D. immitis*-associated antibodies formed in response to adult *D. immitis* infection. The present invention takes advantage of this serological anomaly to provide for significantly enhanced accuracy in serological detection of canine dirofilariasis.

The following examples illustrate practice of the invention and more specifically relate to preparation of the *T. canis*-derived antigen treatment agent; preparation of the semi-purified *D. immitis*-associated antigen used in immunological assays; and performance of an ELISA assay for quantitative detection of adult *D. immitis*-associated antibody. The examples include the use of certain abbreviations: "ELISA" shall mean enzyme linked immunosorbent assay. "PBSS-T20" shall mean a 0.05% solution of Tween 20 in phosphate buffered saline solution. "Enzyme antibody conjugate" shall mean horseradish peroxidase-conjugated rabbit anti-canine Immunoglobulin G. "Substrate solution" shall mean 0.4 millimolar 2,2'-azino-di-(3-ethylbenzthiazoline sulfonic acid) and 2 millimolar hydrogen peroxide diluted to final molarity in 0.05M citrate buffer (pH 4.0). "TCA" shall mean 10% trichloroacetic acid.

Infected serum for the assays was obtained from pedigreed Beagle dogs, 9 to 10 months old, inoculated subcutaneously in the inguinal region with *D. immitis* infective larvae.

EXAMPLE I

*T. canis*-derived antigen preparations may be obtained by the following procedure.

Adult *T. canis* worms are comminuted with scalpel blades and homogenized at 4° C. for up to 30 minutes in a tissue homogenizer with Tris buffer (pH 8.0) in an amount approximately five times the volume of the worm fragments. This homogenate is extracted for 24 to 48 hours and then centrifuged at 12,500 times gravity for 30 minutes and the resultant supernatant is harvested. The crude *T. canis*-derived antigen supernatant is characterized as containing approximately six milligrams of protein per milliliter as based on $A_{280}$ units.

EXAMPLE II

Adult *D. immitis*-associated antigen was semi-purified for use in immunological assays according to the general procedures set out in Montovani et al., *Am. J. Vet. Res.*, 28, pp. 311–317 (1967). More specifically, antigen is obtained from adult *D. immitis* worms by separating males and females, (comminuting and homogenizing the separate fractions) and then extracting them independently in 0.05M tris buffer pH 8. An equivalent amount of extract (based on $A_{280}$ units) from each of these preparations is combined as the initial crude antigen preparation. TCA is added to the antigen until the pH of the solution reaches 3.5–3.6. The TCA soluble solution is exhaustively dialyzed against distilled water and then separated on a Sephadex G-100 column. Two major peaks become apparent; the second peak to elute is subjected to cation exchange chromatography. This preparation is dialyzed against 0.005M acetate buffer (pH 4.6) and applied to a Carboxymethyl Sephadex C-50 column. Extract that is bound to the column with the starting buffer is sequentially eluted with 0.05M phosphate buffer (pH 7), 0.1M NaCl (pH 7), 0.2M, NaCl (pH 7), 0.4M NaCl (pH 7) and 0.11M NaOH (pH 7). The fraction that elutes with 0.2M NaCl is dialyzed and diluted (5 µg of protein/ml) with 0.1M carbonate buffer (pH 9.6), and used as the semipurified serologic antigen. Using Polyacrylamide Gel Electrophoresis in a sodium dodecyl sulfate buffer system, the semi-purified antigen is characterized by at least six identifiable protein-staining bands [Coomassie Brilliant Blue Stain] with approximate molecular weights of 78,000; 30,000; 27,000; 18,500; 17,000; and 16,000.

EXAMPLE III

An ELISA embodying the improvement of the invention for quantitative detection of adult *D. immitis*-associated antibody in the serum of infected dogs involved the following procedures:

50 µl of diluted antigen solution of Example II was added to each well of a polystyrene Microtiter plate. The plates were dried at 37° C. for 3 hours and stored at room temperature. Immediately before use, all wells were washed 3 times (3 minutes for each wash) with PBSS-T20 (pH 7.4). After the final wash, 50 μl of PBSS-T20 was added to each well as a diluent for serum dilutions.

Before diluting the serum, 50 μl of each serum sample was absorbed for 20 minutes at room temperature with 20 μl of a crude soluble somatic *Toxocara canis*-derived antigen of Example I (approximately 6.0 mg of protein/ml). Each absorbed serum (50 μl) was serially diluted 12 times in a Microtiter plate containing adsorbed *D. immitis*-associated antigen with a 50-μl diluter, then incubated at room temperature for 15 minutes. Exposure of *D. immitis*-associated antigen to *D. immitis*-associated antibody in the serum resulted in conjugates of antigen to antibody. After incubation, each well was washed 3 times in PBSS-T20 (3 minutes each wash). Washing removed the excess serum but left behind the antigen-antibody conjugates and the remaining absorbed antigen which was in excess of available antibody in the serum.

Upon completion of the final wash, 50 μl of enzyme-antibody conjugate diluted 1:2,000 in PBSS-T20, was added to each well. After incubation at room temperature for 15 minutes, the residual conjugate was removed by washing each well 3 times in PBSS-T20 (3 minutes each wash). Because the antibody in the conjugate is rabbit anti-dog antibody, it attaches to the antigen-antibody complexes in the well, forming antigen-antibody-antibody-enzyme "sandwiches." Antigen in the well which was unabsorbed by serum sample antibody is not affected by the presence of conjugate. After the last wash, 100 μl of substrate solution was added to each well. The substrate now present in the well is acted upon by the enzyme in the "sandwiches", producing a color change. The more *D. immitis*-associated antibody present in the serum which formed the enzyme-antibody conjugate "sandwich", the greater the color change. Each plate was agitated periodically until the substrate converted adequately to give optimum color development. End points were determined visually. A known positive and a known negative serum sample were used on each plate to ensure consistency between plates.

Other parameters for the *T. canis* treatment which may be successfully used in this procedure are contained in the following Table I.

TABLE I

| *T. canis* antigen to serum ratio | Incubation Time | Incubation Temperature |
|---|---|---|
| 1:3 | 18 hr | 4° C. |
| 1:3 | 2 hr | 36° C. |
| 1:3 | 20 min | room temp. (approx. 28° C.) |
| 2:5 | 18 hr | 4° C. |
| 2:5 | 2 hr | 36° C. |
| 2:5 | 20 min | room temp. |
| 2:5 | 5 min | room temp. |

EXAMPLE IV

Two studies were conducted using an ELISA including *T. canis* antigen treatment as described in Example III. A total of 38 dogs were involved in the studies including, in addition to uninfected controls, experimentally infected animals which were either left untreated or treated with diethylcarbamazine commencing 5 days before infection. Briefly summarized, the ELISA procedure according to the invention was effective in ascertaining significant serological distinctiveness between infected and noninfected animals at about 16 weeks into the test period, fully 10 to 14 weeks before any distinction could be made on the basis of parasitological detection of circulating microfilariae. The ELISA was able to serologically distinguish between drug-treated and untreated dogs on the basis of anti-*D. immitis* antibodies at about 13 weeks, again from 13 to 15 weeks before any distinction could be had by parasitological determination.

EXAMPLE V

Treating the serum with *T. canis*-derived antigen removes most of the background experienced in assays for *D. immitis*-associated antibody when serum is unabsorbed. By absorbing out non-specific antibody which would otherwise react with the *D. immitis*-associated antigen of the assay, the *T. canis* absorption improves the accuracy of *D. immitis* infection diagnosis by preventing false positives in negative sera and by defining endpoints of *D. immitis* infection levels more clearly in positive sera.

The following pattern has been continuously demonstrated, comparing anti-*D. immitis* titers in sera of non-infected and infected dogs with and without the *T. canis* treatment step.

When assayed for anti-*D. immitis* titer, sera of dogs known to be non-infected produce titers of approximately 1:32 to 1:64, indicating an infection revealed by the presence of some *D. immitis*-associated antibody. Sera of known infected dogs produce titers of anti-*D. immitis*-associated antibody of approximately 1:256 to 1:512, indicating high levels of infection. When these same sera samples are treated with the *T. canis*-derived antigen method of the present invention, titers of the non-infected animals drop to approximately 1:4, demonstrating that the animals are truly non-infected. Sera of the known positively infected dogs show very small to no reduction in titer levels. Thus, the treatment step serves the dual functions of eliminating the cross-reaction of non-specific antibodies which can indicate false positive diagnoses in non-infected animals, and establishing the true endpoints of antibody level in infected animals.

Because the present invention involves the improvement of immunological assays for *D. immitis*-associated antibody, it will be apparent that the procedural steps in the assays and purification schemes described in the above examples are only included for illustration and may be varied. If needed, for example, *T. canis* absorption as well as serum and conjugate incubations and washing times in the ELISA may be significantly shortened, especially if conjugate concentrations are correspondingly increased to allow for easier "readability" of the assay.

Among the more significant alterations that may be performed in the assays described above is the substitution of enzyme-conjugated Protein A for the rabbit-antidog-antibody used in ELISA and other immunoassays. Protein A, conjugated to an enzyme for ELISA or to a fluorescent label for a fluorescent immunoassay, will perform the same function as the indicator of the amount of *D. immitis*-associated antibody in the sample. As noted earlier, the treatment step of the invention is equally applicable to, and does not interfere with, immunological assays performed on anticoagulant-treated whole blood. Whole blood is significantly more readily handled in routine veterinary diagnostic procedures.

What is claimed is:

1. In an immunological method for the quantitative detection of adult *Dirofilaria immitis*-associated antibodies in a fluid sample of canine origin wherein said sample is contacted with adult *Dirofilaria immitis*-associated antigen and *Dirofilaria immitis* antibodies in said sample are determined on the basis of a selective immunological reaction with said antigen, the improvement comprising:

treating said sample, prior to contact with *Dirofilaria immitis* antigen, with a soluble *Toxocara canis*-derived antigen preparation non-immunologically reactive with *Dirofilaria immitis* antibodies, but capable of selectively immunologically reacting with antibodies in said sample which are cross-reactive with *Dirofilaria immitis* antigen.

2. A method according to claim 1 wherein said fluid sample is whole blood.

3. A method according to claim 1 wherein said fluid sample is serum.

4. An immunological process for the quantitative detection of adult *Dirofilaria immitis*-associated antibodies in a fluid sample of canine origin wherein said sample is contacted with adult *Dirofilaria immits*-associated antigen and *Dirofilaria immitis* antibodies in said sample are determined on the basis of a selective immunological reaction with said antigen, said process comprising:

treating said sample, prior to contact with *Dirofilaria immitis* antigen with a soluble *Toxocara canis*-derived antigen preparation non-immunologically reactive with *Dirofilaria immitis* antibodies capable of selectively immunologically reacting with antibodies in said sample which are cross-reactive with *Dirofilaria immitis* antigen in an enzyme linked immunosorbent assay.

* * * * *